US012605044B2

(12) United States Patent
Hsu

(10) Patent No.: US 12,605,044 B2
(45) Date of Patent: Apr. 21, 2026

(54) ENDOSCOPE MODULE

(71) Applicant: Chicony Electronics Co., Ltd., New Taipei City (TW)

(72) Inventor: Cheng-Lung Hsu, New Taipei City (TW)

(73) Assignee: Chicony Electronics Co., Ltd., New Taipei City (TW)

( * ) Notice: Subject to any disclaimer, the term of this patent is extended or adjusted under 35 U.S.C. 154(b) by 353 days.

(21) Appl. No.: 18/311,899

(22) Filed: May 4, 2023

(65) Prior Publication Data

US 2024/0180399 A1      Jun. 6, 2024

(30) Foreign Application Priority Data

Dec. 2, 2022    (TW) .................................. 111146464

(51) Int. Cl.
A61B 1/00          (2006.01)
A61B 1/05          (2006.01)
A61B 1/06          (2006.01)

(52) U.S. Cl.
CPC .............. A61B 1/0008 (2013.01); A61B 1/05 (2013.01); A61B 1/0676 (2013.01)

(58) Field of Classification Search
CPC .................. A61B 1/00114; A61B 1/05; A61B 1/06–0684; H04N 23/555; H04N 23/54; H04N 23/50
See application file for complete search history.

(56) References Cited

U.S. PATENT DOCUMENTS 10,925,471 B2      2/2021  Salman et al.
2011/0242302 A1*  10/2011  Jacobsen ................ H04N 23/50
                                                        359/599
2017/0127915 A1*   5/2017  Viebach ................. A61B 1/018
2023/0165449 A1*   6/2023  Chung .................... A61B 1/05
                                                        600/109

FOREIGN PATENT DOCUMENTS

TW          202218617 A      5/2022

* cited by examiner

*Primary Examiner* — Alexandra L Newton
(74) *Attorney, Agent, or Firm* — CKC & Partners Co., LLC

(57)          ABSTRACT

An endoscope module includes a non-metallic main body, a plurality of lighting devices and an image-obtaining device. The non-metallic main body includes a body and a plurality of extending portions. The body has a first surface. The extending portions are respectively connected with the first surface. The extending portions define a space therebetween. The lighting devices are respectively disposed on a side of a corresponding one of the extending portions away from the first surface. Each of the lighting devices has a light-emitting surface located on a side of a corresponding one of the lighting devices away from the first surface. The image-obtaining device is at least partially located in the space and connected with the first surface. The image-obtaining device has a light-transmitting surface located on a side of the image-obtaining device away from the first surface.

8 Claims, 5 Drawing Sheets

ENDOSCOPE MODULE

RELATED APPLICATIONS

This application claims priority to Taiwanese Application Serial Number 111146464 filed Dec. 2, 2022, which is herein incorporated by reference.

BACKGROUND

Technical Field

The present disclosure relates to endoscope modules.

Description of Related Art

With the continuous advancement of medical science nowadays, the demand of people for medical standards is becoming higher and higher. In practice, in addition to the research and development of diversified medicines, the efficiency and safety of operations are also areas which people concern.

For example, for medical devices which are used inside the human bodies during operations, people naturally hope that the volume of such devices should be as small as possible, and these medical devices preferably have dimensions of high precision to avoid medical accidents.

SUMMARY

A technical aspect of the present disclosure is to provide an endoscope module, which can enhance the structural strength and achieve accurate dimensions of the endoscope module, facilitating the light-transmitting surface of the image-obtaining device and the light-emitting surfaces of the lighting devices to be coplanar with each other in a simple and easy manner.

According to an embodiment of the present disclosure, an endoscope module includes a non-metallic main body, a plurality of lighting devices and an image-obtaining device. The non-metallic main body includes a body and a plurality of extending portions. The body has a first surface. The extending portions are respectively connected with the first surface. The extending portions define a space therebetween. The lighting devices are respectively disposed on a side of a corresponding one of the extending portions away from the first surface. Each of the lighting devices has a light-emitting surface located on a side of a corresponding one of the lighting devices away from the first surface. The image-obtaining device is at least partially located in the space and connected with the first surface. The image-obtaining device has a light-transmitting surface located on a side of the image-obtaining device away from the first surface.

In one or more embodiments of the present disclosure, the light-transmitting surface and the light-emitting surfaces are coplanar with each other.

In one or more embodiments of the present disclosure, the extending portions respectively extend along an extension direction to form a columnar shape. Each of the extending portions has a cross-sectional area. The extension direction is perpendicular to the cross-sectional area and the first surface. A projection of each of the lighting devices along the extension direction is smaller than a corresponding one of the cross-sectional areas.

In one or more embodiments of the present disclosure, the body and the extending portions are of an integrally-formed structure.

In one or more embodiments of the present disclosure, the non-metallic main body is plastic.

In one or more embodiments of the present disclosure, the image-obtaining device and the extending portions are separated from each other.

In one or more embodiments of the present disclosure, each of the lighting devices includes a light source and a colloid. The light source is connected between the colloid and a corresponding one of the extending portions. The light-emitting surface is located at a side of the colloid away from the light source. The light source is configured to emit a light ray towards the colloid and the light ray penetrates through the light-emitting surface to leave from the colloid.

In one or more embodiments of the present disclosure, each of the colloids is hypoallergenic material.

In one or more embodiments of the present disclosure, the body has a plurality of through holes, a second surface and a third surface opposite to the second surface. The first surface is connected between the second surface and the third surface. The through holes respectively are communicated between the second surface and the third surface. The non-metallic main body further includes a plurality of first lines, a plurality of second lines and a plurality of conductive pillars. The first lines are disposed on the second surface and connected with the image-obtaining device and the lighting devices. The second lines are disposed on the third surface and connected with the image-obtaining device and the lighting devices. The conductive pillars are located inside the through holes and respectively connected with a corresponding one of the first lines and a corresponding one of the second lines.

In one or more embodiments of the present disclosure, the non-metallic main body further includes a plurality of conductive pads. The conductive pads are disposed on the third surface and connected with the second lines. The endoscope module further includes at least one capacitor. The capacitor is disposed on the second surface and connected with the first lines.

The above-mentioned embodiments of the present disclosure have at least the following advantages:

(1) Since the body and the extending portions are of an integrally-formed structure, the structural strength of the non-metallic main body is effectively enhanced. Moreover, the non-metallic main body can be made by laser direct structuring or injection molding. Thus, the non-metallic main body can achieve accurate dimensions.

(2) Under the conditions that a length of the image-obtaining device along the extension direction, a length of the colloids along the extension direction and a length of the light sources along the extension direction are known, a user can apply laser direct structuring or injection molding to make the non-metallic main body, such that the extending portions have an appropriate and accurate length. In this way, after the image-obtaining device and the lighting devices are installed on the non-metallic main body, the light-transmitting surface of the image-obtaining device and the light-emitting surfaces of the lighting devices can be coplanar with each other.

(3) Through the first lines disposed on the second surface of the body and the second lines disposed on the third surface of the body, apart from a better utilization of space, the problems related to width of each of the lines and interval(s) between lines can be effectively avoided.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
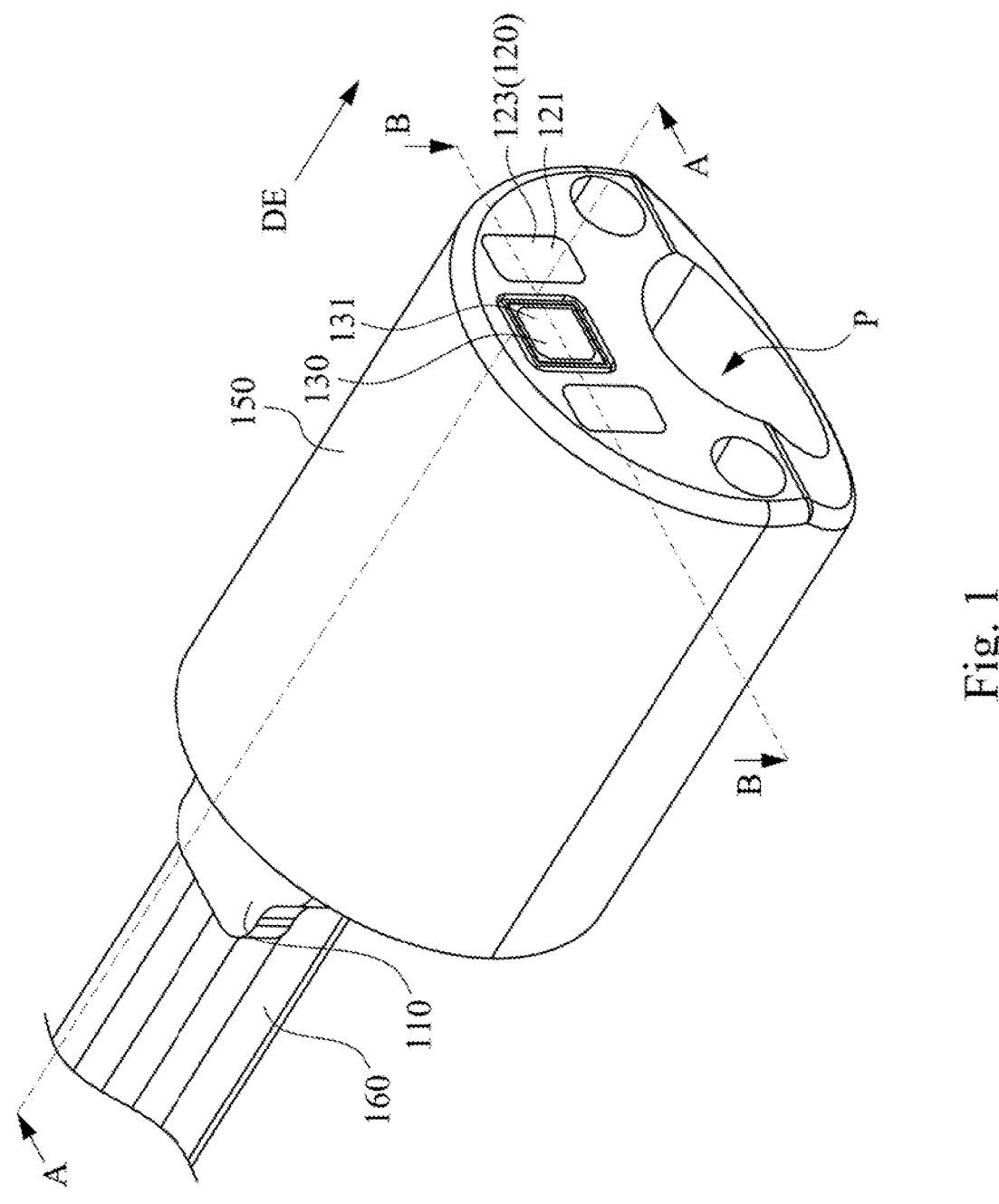
FIG. 1 is a schematic view of an endoscope module according to an embodiment of the present disclosure.

Drawings will be used below to disclose embodiments of the present disclosure. For the sake of clear illustration, many practical details will be explained together in the description below. However, it is appreciated that the practical details should not be used to limit the claimed scope. In other words, in some embodiments of the present disclosure, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meanings as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
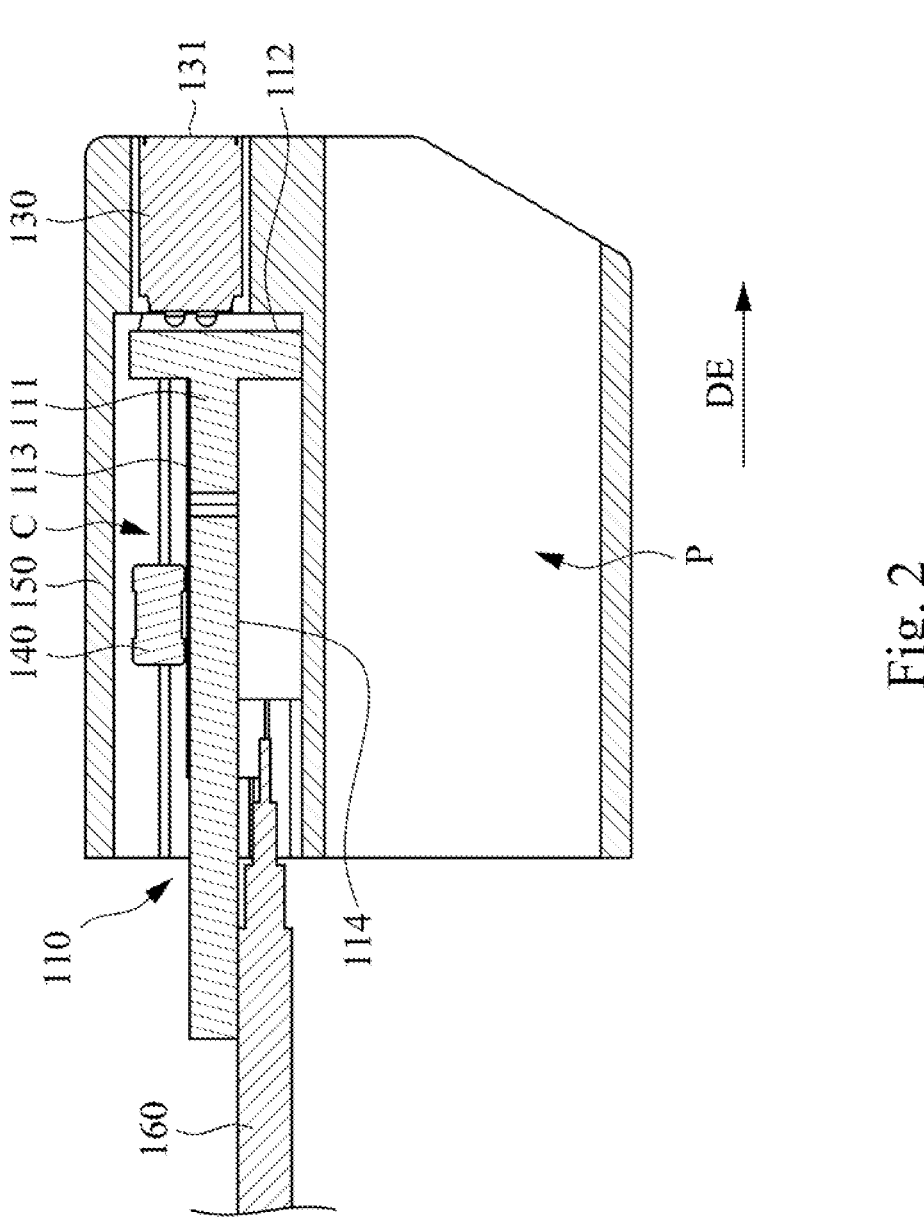
FIG. 2 is a cross-sectional view along the section line A-A of FIG. 1.

Reference is made to FIGS. 1-2. FIG. 1 is a schematic view of an endoscope module 100 according to an embodiment of the present disclosure. FIG. 2 is a cross-sectional view along the section line A-A of FIG. 1. In this embodiment, as shown in FIGS. 1-2, an endoscope module 100 includes a housing 150, a non-metallic main body 110 and a cable 160. The housing 150 has a chamber C and a through hole P. The chamber C is adjacent to the through hole P. The through hole P extends along an extension direction DE. The through hole P is configured to allow a medical tool (not shown) to penetrate through. The non-metallic main body 110 is at least partially disposed in the chamber C of the housing 150, and the cable 160 is connected with the non-metallic main body 110.

Figure 3:
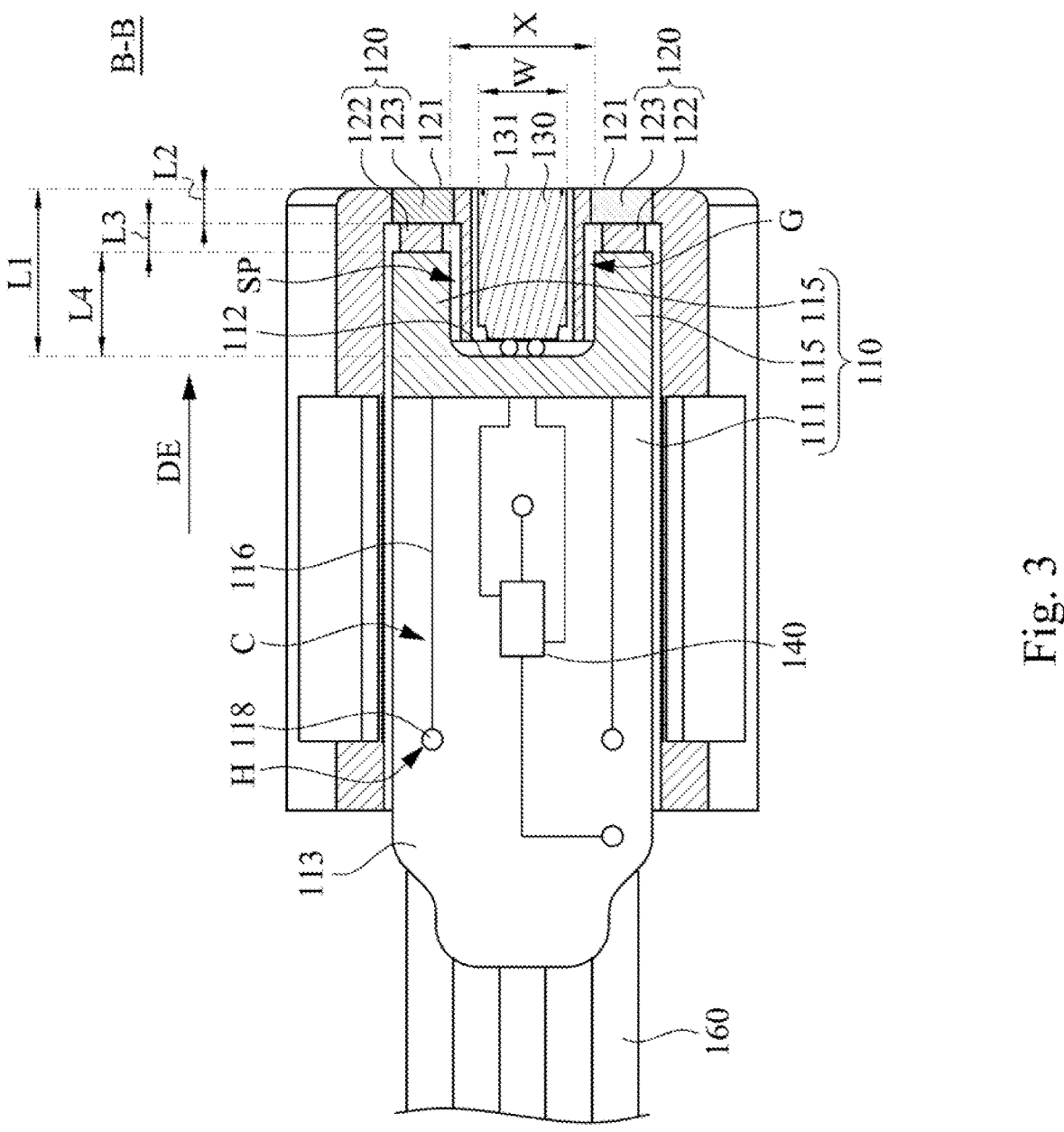
FIG. 3 is a cross-sectional view along the section line B-B of FIG. 1.

Reference is made to FIG. 3. FIG. 3 is a cross-sectional view along the section line B-B of FIG. 1. In this embodiment, the non-metallic main body 110 includes a body 111 and a plurality of extending portions 115. To be specific, as shown in FIG. 3, a quantity of the extending portions 115 is two. The body 111 of the non-metallic main body 110 has a first surface 112, and the extending portions 115 are respectively connected with the first surface 112. The extending portions 115 define a space SP therebetween. Moreover, the endoscope module 100 further includes a plurality of lighting devices 120 and an image-obtaining device 130. To be specific, as shown in FIG. 3, a quantity of the lighting devices 120 is also two. The lighting devices 120 are respectively disposed on a side of a corresponding one of the extending portions 115 away from the first surface 112, and each of the lighting devices 120 has a light-emitting surface 121. The light-emitting surface 121 is located on a side of the lighting device 120 away from the first surface 112. Each of the lighting devices 120 emits a light ray through the light-emitting surface 121 to achieve the effect of lighting. The image-obtaining device 130 is at least partially located in the space SP and directly connected with the first surface 112 of the body 111. The image-obtaining device 130 has a light-transmitting surface 131. The light-transmitting surface 131 is located on a side of the image-obtaining device 130 away from the first surface 112. To be specific, the light-transmitting surface 131 can be, for example, a surface of a lens, and the image-obtaining device 130 can obtain an image through the light-transmitting surface 131.

It is worth to note that, in this embodiment, the light-transmitting surface 131 of the image-obtaining device 130 and the light-emitting surfaces 121 of the lighting devices 120 are coplanar with each other. The light-transmitting surface 131 and the light-emitting surfaces 121 are all exposed from the housing 150 and aligned with an outer surface of the housing 150. Since the light-transmitting surface 131 and the light-emitting surfaces 121 are coplanar with each other, there is no height difference between the light-transmitting surface 131 and the light-emitting surfaces 121 along the extension direction DE. Therefore, the area to be illuminated is avoided from appearance of any shadow, which facilitates the image-obtaining device 130 to obtain clear images.

In practical applications, the body 111 and the extending portions 115 are of an integrally-formed structure. Therefore, the structural strength of the non-metallic main body 110 is effectively enhanced. For example, the non-metallic main body 110 is applied plastic material of laser direct structuring (LDS), or the non-metallic main body 110 is made by injection molding. Thus, the non-metallic main body 110 can achieve accurate dimensions.

Furthermore, as shown in FIG. 3, a distance X between the extending portions 115 is larger than a width W of the image-obtaining device 130. In other words, the image-obtaining device 130 and the extending portions 115 are separated from each other and do not contact with each other. This means that there exists a gap G between the image-obtaining device 130 and each of the extending portions 115, which effectively simplifies the process to install the image-obtaining device 130 on the non-metallic main body 110.

To be more specific, as shown in FIG. 3, each of the lighting devices 120 includes a light source 122 and a colloid 123. The light source 122 is connected between the colloid 123 and the extending portion 115 of the non-metallic main body 110. The light-emitting surface 121 is located at a side of the colloid 123 away from the light source 122. The light source 122 is configured to emit a light ray towards the colloid 123 and the light ray penetrates through the light-emitting surface 121 to leave from the colloid 123, in order to achieve the effect of lighting, which facilitates the image-obtaining device 130 to obtain clear images. In practical applications, the light sources 122 are light-emitting diodes, and the colloids 123 are of hypoallergenic material, such as biocompatible optically clear ultraviolet (UV) glue, which avoids the risk of allergy inside the human body caused by the endoscope module 100.

In practical applications, under the conditions that a length L1 of the image-obtaining device 130 along the extension direction DE, a length L2 of the colloids 123 along the extension direction DE and a length L3 of the light sources 122 along the extension direction DE are known, a user can apply laser direct structuring or injection molding to make the non-metallic main body 110, such that the extending portions 115 have an appropriate and accurate length L4. In this way, after the image-obtaining device 130 and the lighting devices 120 are installed on the non-metallic main body 110, the light-transmitting surface 131 of the image-obtaining device 130 and the light-emitting surfaces 121 of the lighting devices 120 can be coplanar with each other.

For example, when the length L1 of the image-obtaining device 130 along the extension direction DE is known to be 1.198 mm, the length L2 of the colloids 123 along the extension direction DE is known to be 0.25 mm, and the length L3 of the light sources 122 along the extension direction DE is known to be 0.2 mm, a user can set the length L4 of the extending portions 115 along the extension direction DE to be 0.748 mm, such that the light-transmitting surface 131 of the image-obtaining device 130 and the light-emitting surfaces 121 of the lighting devices 120 are coplanar with each other. However, it is noted that the dimensions as cited herein are only illustrative and are not to limit the claimed scope. A person having ordinary skill in the art of the present disclosure may appropriately choose the dimensions of the image-obtaining device 130, the colloids 123, the light sources 122 and the extending portions 115, according to the actual situations.

Figure 4:
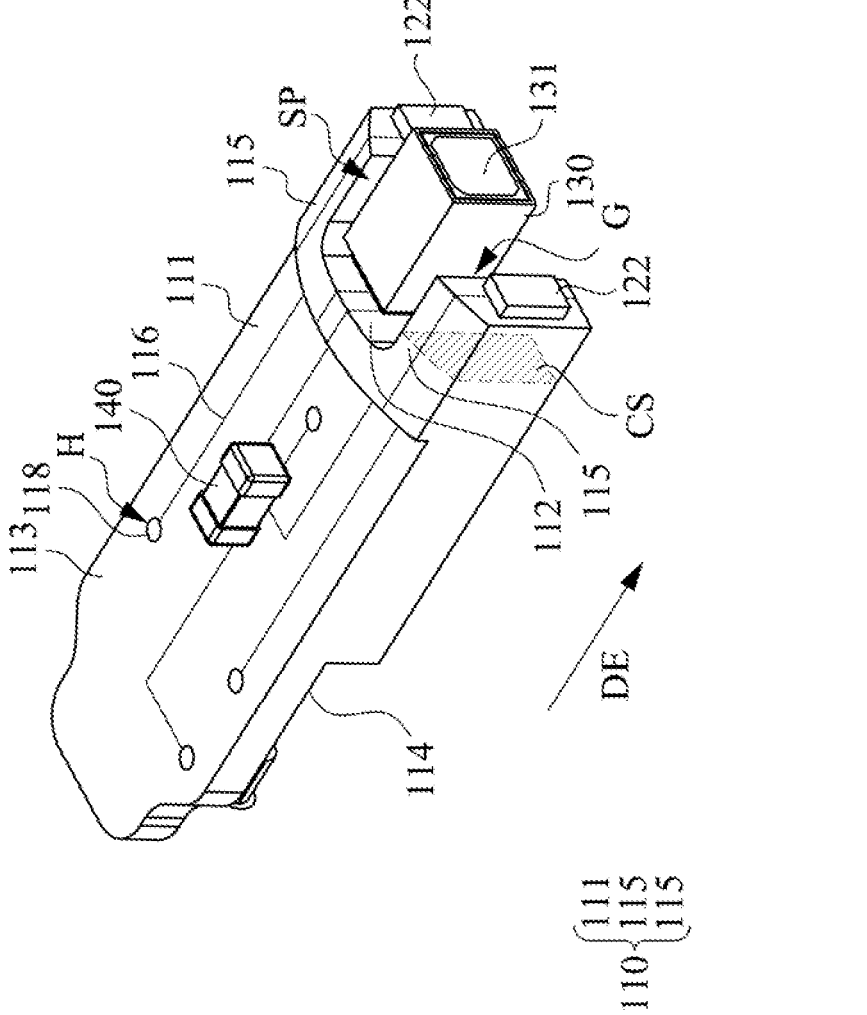
FIG. 4 is a schematic bottom view of the non-metallic main body of FIGS. 2-3, in which the colloids are not shown.
Figure 5:
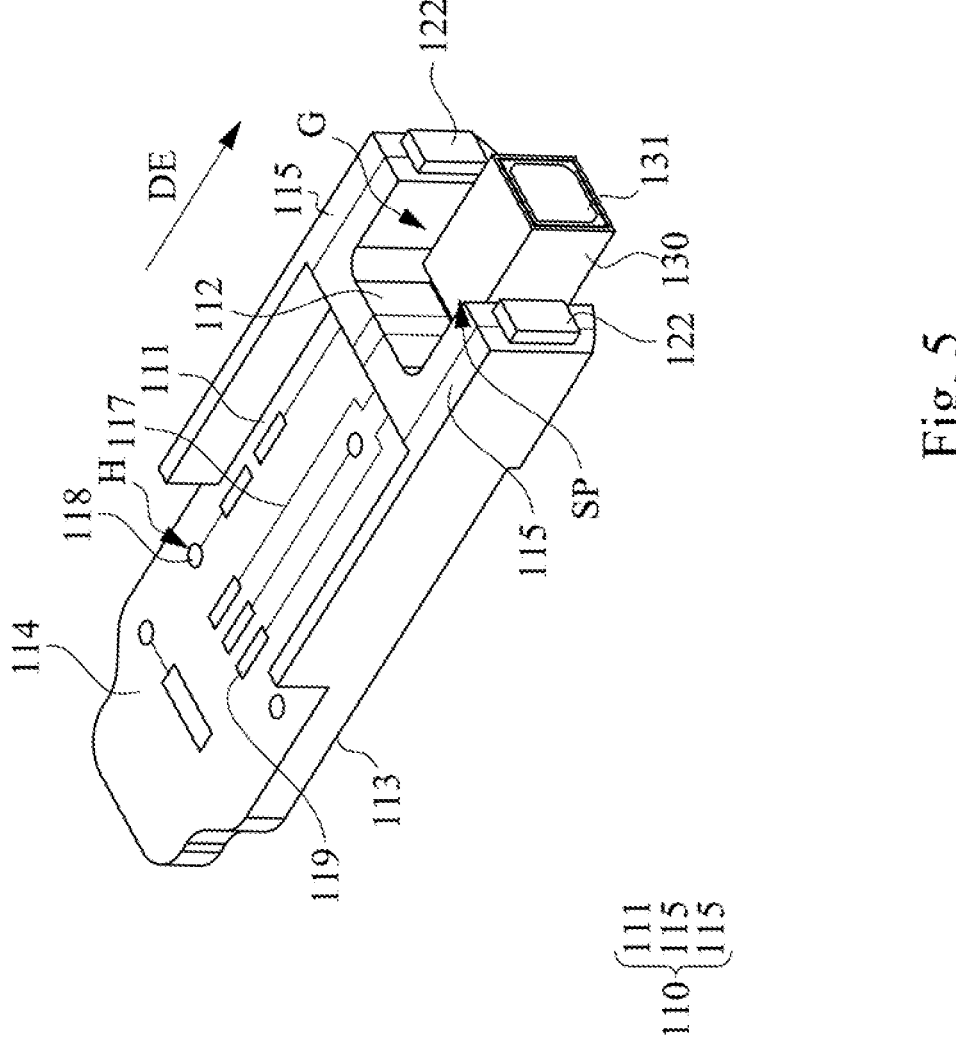
FIG. 5 is a schematic top view of the non-metallic main body of FIGS. 2-3, in which the colloids are not shown.

Reference is made to FIGS. 4-5. FIGS. 4-5 are respectively schematic bottom view and schematic top view of the non-metallic main body 110 of FIGS. 2-3, in which the colloids 123 are not shown. In this embodiment, as shown in FIGS. 4-5, the extending portions 115 respectively extend along the extension direction DE to form a columnar shape. Since the extending portions 115 and the body 111 are of an integrally-formed structure, each of the extending portions 115 has a strong structural strength. Moreover, each of the extending portions 115 has a cross-sectional area CS (please see FIG. 4). The cross-sectional areas CS are parallel with the first surface 112 of the body 111, and the extension direction DE is perpendicular to the cross-sectional areas CS and the first surface 112. A projection of each of the lighting devices 120 along the extension direction DE is smaller than a corresponding one of the cross-sectional areas CS. This means that an area of each of the cross-sectional areas CS is larger than an area of the projection of a corresponding one of the lighting devices 120 along the extension direction DE.

In addition, as shown in FIGS. 4-5, the body 111 of the non-metallic main body 110 has a plurality of through holes H, a second surface 113 and a third surface 114 opposite to the second surface 113. The first surface 112 is connected between the second surface 113 and the third surface 114. The through holes H are respectively communicated between the second surface 113 and the third surface 114. Moreover, the non-metallic main body 110 further includes a plurality of first lines 116, a plurality of second lines 117 and a plurality of conductive pillars 118. The first lines 116 are disposed on the second surface 113, for example through the application of chemical plating, and connected with the image-obtaining device 130 and the lighting devices 120. Similarly, the second lines 117 are disposed on the third surface 114, for example through the application of chemical plating, and connected with the image-obtaining device 130 and the lighting devices 120. The conductive pillars 118 are located inside the through holes H and respectively connected with a corresponding one of the first lines 116 and a corresponding one of the second lines 117. For example, the first lines 116 are negative lines while the second lines 117 are positive lines. However, this does not intend to limit the present disclosure. Through the first lines 116 disposed on the second surface 113 of the body 111 and the second lines 117 disposed on the third surface 114 of the body 111, apart from a better utilization of space, the problems related to width of each of the lines and interval(s) between lines can be effectively avoided.

In practical applications, as shown in FIG. 5, the non-metallic main body 110 further includes a plurality of conductive pads 119. The conductive pads 119 are disposed on the third surface 114 and connected with the second lines 117. The conductive pads 119 are configured to electrically connect with the cable 160 (please see FIGS. 1-3), such that the cable 160 is electrically connected with the image-obtaining device 130 and the lighting devices 120. Moreover, as shown in FIG. 4, the endoscope module 100 further includes at least one capacitor 140. The capacitor 140 is disposed on the second surface 113 and connected with the first lines 116.

In conclusion, the aforementioned embodiments of the present disclosure have at least the following advantages:

(1) Since the body and the extending portions are of an integrally-formed structure, the structural strength of the non-metallic main body is effectively enhanced. Moreover, the non-metallic main body can be made by laser direct structuring or injection molding. Thus, the non-metallic main body can achieve accurate dimensions.

(2) Under the conditions that a length of the image-obtaining device along the extension direction, a length of the colloids along the extension direction and a length of the light sources along the extension direction are known, a user can apply laser direct structuring or injection molding to make the non-metallic main body, such that the extending portions have an appropriate and accurate length. In this way, after the image-obtaining device and the lighting devices are installed on the non-metallic main body, the light-transmitting surface of the image-obtaining device and the light-emitting surfaces of the lighting devices can be coplanar with each other.

(3) Through the first lines disposed on the second surface of the body and the second lines disposed on the third surface of the body, apart from a better utilization of space, the problems related to width of each of the lines and interval(s) between lines can be effectively avoided.

Although the present disclosure has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. An endoscope module, comprising:
   a housing;
   a non-metallic main body at least partially disposed in the housing, the non-metallic main body comprising:
      a body having a first surface; and a plurality of extending portions respectively connected with the first surface, the extending portions defining a space therebetween;

a plurality of lighting devices, each of the lighting devices comprising:

a light source; and a colloid, the light source being connected between the colloid and a side of a corresponding one of the extending portions away from the first surface, the colloid being spaced apart from the said one of the extending portions, a lateral surface of the light source being free from contact with the colloid, the colloid having a light-emitting surface away from the light source and exposed from the housing, the light source being configured to emit a light ray towards the colloid and the light ray penetrating through the light-emitting surface to leave from the colloid; and an image-obtaining device at least partially located in the space and connected with the first surface, the image-obtaining device having a light-transmitting surface located on a side of the image-obtaining device away from the first surface and exposed from the housing, a portion of the housing at least partially isolating a corresponding one of the colloids and a corresponding one of the light sources from the image-obtaining device, wherein each of the colloids is hypoallergenic material.

2. The endoscope module of claim 1, wherein the light-transmitting surface and the light-emitting surfaces are coplanar with each other.

3. The endoscope module of claim 1, wherein the extending portions respectively extend along an extension direction to form a columnar shape, each of the extending portions has a cross-sectional area, the extension direction is perpendicular to the cross-sectional area and the first surface, a projection of each of the lighting devices along the extension direction is smaller than a corresponding one of the cross-sectional areas.

4. The endoscope module of claim 1, wherein the body and the extending portions are of an integrally-formed structure.

5. The endoscope module of claim 1, wherein the non-metallic main body is plastic.

6. The endoscope module of claim 1, wherein the image-obtaining device and the extending portions are separated from each other.

7. The endoscope module of claim 1, wherein the body has a plurality of through holes, a second surface and a third surface opposite to the second surface, the first surface is connected between the second surface and the third surface, the through holes respectively are communicated between the second surface and the third surface, the non-metallic main body further comprises:

a plurality of first lines disposed on the second surface and connected with the image-obtaining device and the lighting devices;

a plurality of second lines disposed on the third surface and connected with the image-obtaining device and the lighting devices; and a plurality of conductive pillars located inside the through holes and respectively connected with a corresponding one of the first lines and a corresponding one of the second lines.

8. The endoscope module of claim 7, wherein the non-metallic main body further comprises:

a plurality of conductive pads disposed on the third surface and connected with the second lines, the endoscope module further comprises:

at least one capacitor disposed on the second surface and connected with the first lines.

* * * * *